(12) United States Patent
Gibson

(10) Patent No.: US 8,592,655 B2
(45) Date of Patent: Nov. 26, 2013

(54) SUN QUEST LETTUCE VARIETY

(75) Inventor: George D. Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 302 days.

(21) Appl. No.: 13/052,521

(22) Filed: Mar. 21, 2011

(65) Prior Publication Data

US 2012/0073022 A1    Mar. 22, 2012

Related U.S. Application Data

(60) Provisional application No. 61/320,677, filed on Apr. 2, 2010.

(51) Int. Cl.
*A01H 5/00* (2006.01)
*A01H 5/10* (2006.01)
*C12N 5/04* (2006.01)

(52) U.S. Cl.
USPC .......................... 800/305; 800/260; 435/410

(58) Field of Classification Search
None
See application file for complete search history.

(56) References Cited

U.S. PATENT DOCUMENTS 7,977,536 B2 *   7/2011   Holland et al. ............... 800/305

* cited by examiner

*Primary Examiner* — Eileen B O Hara
(74) *Attorney, Agent, or Firm* — Morrison & Foerster LLP

(57) ABSTRACT

A new lettuce variety designated Sun Quest is described. Sun Quest is an iceberg lettuce variety exhibiting stability and uniformity.

7 Claims, 1 Drawing Sheet

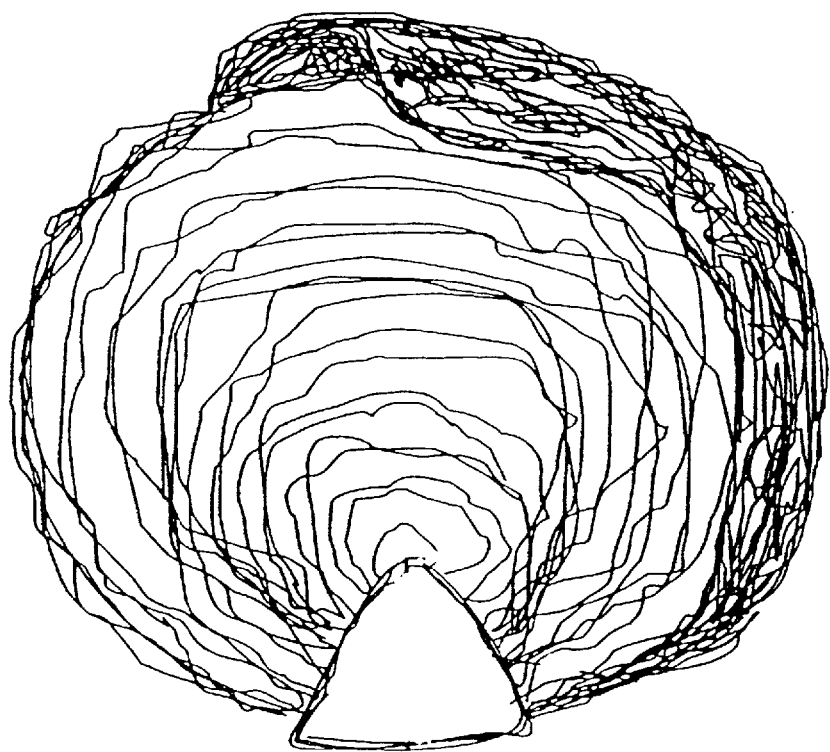

under the invention are part of the invention. The invention is further directed to the lettuce variety, Sun Quest, having ATCC Accession Number PTA-11798.

SUN QUEST LETTUCE VARIETY

I. CROSS REFERENCE TO RELATED APPLICATIONS

This application claims the benefit under 35 USC 119(e) of prior U.S. Provisional Patent Application No. 61/320,677, filed Apr. 2, 2010, the disclosure of which is hereby incorporated by reference in its entirety.

II. FIELD OF THE INVENTION

This invention relates to the field of plant breeding. In particular, this invention relates to a new lettuce, *Lactuca sativa*, variety, Sun Quest.

III. BACKGROUND OF THE INVENTION

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

IV. SUMMARY OF THE INVENTION

In order to meet these needs, the present invention is directed to an improved iceberg lettuce variety that exhibits vigorous growth, increased weight and yield. In particular, the present invention is directed to *Lactuca sativa* seed designated as Sun Quest having ATCC Accession Number PTA-11798. The present invention is further directed to a *Lactuca sativa* plant produced by growing Sun Quest lettuce seed having ATCC Accession Number PTA-11798. The present invention is further directed to a *Lactuca sativa* plant having all the physiological and morphological Characteristics of a *Lactuca sativa* plant produced by growing Sun Quest lettuce seed having ATCC Accession Number PTA-11798. The present invention is further directed to an $F_1$ hybrid *Lactuca sativa* plant having Sun Quest as a parent wherein Sun Quest lettuce seed is grown from Sun Quest seed having ATCC Accession Number PTA-11798.

The present invention is further directed to pollen isolated from Sun Quest lettuce plants. The present invention is further directed to tissue culture of Sun Quest lettuce plants.

The present invention is further directed to a method of selecting lettuce comprising a) growing Sun Quest lettuce plants wherein the plants are grown from lettuce seed having ATCC Accession Number PTA-11798 and b) selecting a plant from step a). The present invention is further directed to lettuce plants and seeds produced there from wherein the lettuce plant is isolated by the selection method of the invention.

The present invention is further directed to a method of breeding lettuce comprising crossing a lettuce plant with a plant grown from Sun Quest lettuce seed having ATCC Accession Number PTA-11798. The present invention is further directed to lettuce plants and seeds produced there from wherein the lettuce plant is isolated by the breeding method of the invention.

V. BRIEF DESCRIPTION OF THE FIGURE

The invention will be better understood by reference to FIG. 1 which shows a drawing of cross-section of an iceberg lettuce head showing head length, head diameter, core diameter, core length and a wrapper leaf.

VI. BRIEF DESCRIPTION OF THE TABLES

The invention will be better understood by reference to the Tables in which;

Table 1 shows trial data comparing Sun Devil and Sun Quest iceberg lettuce varieties.

Table 2 shows trial data comparing Sun Devil and Sun Quest iceberg lettuce varieties.

Table 3 shows trial data comparing Sun Devil and Sun Quest iceberg lettuce varieties.

VII. DETAILED DESCRIPTION OF THE INVENTION

In order to more clearly understand the invention, the following definitions are provided:

Iceberg Lettuce Iceberg lettuce, *Lactuca sativa* L. var. capitala L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length Core length is the length of the internal lettuce stem. Core length is measured from the base of the cut head to the tip of the core.

Core Diameter Core diameter is the diameter of the lettuce stem at the base of the cut head.

Head Diameter Head diameter is the diameter of the vertically sliced lettuce plant head at its widest horizontal point, perpendicular to the stem.

Head Length Head length is the diameter of the vertically sliced lettuce plant head as measured from the base of the cut stem to the cap leaf.

Average Head Diameter Average head diameter is an average of the measured head diameter and head length of the lettuce head.

Average Head Diameter: Core Length The ratio of the average head diameter to core length is indicative of the percentage of useable product produced by the lettuce plant.

Frame Diameter The frame diameter is a measurement of the lettuce plant diameter at its widest point. The measurement of frame diameter is from the outer most wrapper leaf tip to outer most wrapper leaf tip.

Head Weight Weight of the marketable lettuce plant, cut and trimmed to market specifications.

Rogueing Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Market Stage Market stage is the stage when a lettuce plant is ready for commercial lettuce harvest. In the case of an iceberg variety, the head is solid, and has reached an adequate size and weight.

Taking into account these definitions, the present invention is directed to seeds of the lettuce variety Sun Quest, plants produced by growing Sun Quest seeds, plants selected from a collection of Sun Quest plants and seeds derived or produced therefrom; plants produced by crossed a lettuce plant with a Sun Quest lettuce plant and seeds derived or produced therefrom.

VIII. ORIGIN AND BREEDING HISTORY OF THE VARIETY SUN QUEST

In year 1, Multiple single plant selections were made from the commercial variety Sun Devil (U.S. Pat. No. 6,495,744) while being grown for commercial seed production in San Joaquin Valley, Calif. Multiple single plant selections were made from the seed production field as part of an extensive stock seed development project. This particular selected plant was 1 of 100, and was a distinct off-type or segregate from the variety Sun Devil exhibiting a distinctively larger head size, and a darker color.

The selected plant, along with multiple other individual plant selections were flagged and the S1 seed was harvested and packaged individually. 100 S1 plants were then again planted in a research and development plot trial in September of year 2 in Yuma, Ariz., in a field where the commercial variety Sun Devil was being grown. The S1 lines were evaluated for uniformity in size, type and maturity, head size, frame size, core length, tip burn resistance, color, leaf texture, days to harvest and field holding ability, as they related to their parent variety Sun Devil. Based on the evaluation, multiple S1 lines were chosen as candidates for the stock seed program for the commercial variety Sun Devil, but 4 S1 lines were noted as unique from the parent variety based on the evaluation criteria.

The S1 line designated PSJV01SDSS-5 as evaluated in the research and development trial was larger heading, larger framed, darker in color, and earlier maturing than the parent variety Sun Devil, while maintaining the desired heavy leaf texture, low core length and tip burn resistance of the parent line. Based on this evaluation PSJV01SDSS-5 along with 3 of its sister lines were advanced as new research lines.

The S1 seed was again trialed in multiple plot trials in year 3 in the September plantings of Yuma, Ariz., where it was again compared to the parent variety Sun Devil.

PSJV01SDSS-5 in both research trials continued to demonstrate the desired improvement traits, being larger heading, larger framed, darker in color and slightly earlier maturing than its parent line, while maintaining the heavy leaf texture and improved tip burn resistance of the variety Sun Devil.

Based on these trial results seed from the S1 line was increased in a year 4 research and development seed production crop in the San Joaquin valley. 500 plants of the S1 line PSJV01SDSS-5 were planted in the seed production field, and grown next to its S1 sister lines, as well as its parent line Sun Devil. PSJV01SDSS-5, now designated PSJV 04 2758 was selectively rogued for size type and maturity, and was noted to be uniform, larger heading, larger framed than Sun Devil at market maturity, and taller and producing a larger seed head at the bolting stage. The S1 line was also slightly earlier maturing than Sun Devil. The S2 seed designated as PSJV 04 2758 was harvested in bulk.

Seed from the S2 increases were planted in multiple research and development plot trials in September of year 5 with its advanced sister lines and the parent variety Sun Devil. The varieties were first evaluated for size, type, and color, and then for tip burn and core length as the plants solidified. The variety PSJV 04 2758 continued to demonstrate the improvement traits, of larger head and frame size, earlier maturing and darker color while maintaining the desired traits of heavy leaf texture, good field holding ability and excellent tip burn resistance. Best on the multiple replicated trial results in year 5 the S2 line PSJV 04 2758 was advanced to PX 1555 in the spring of year 6.

PX 1555 was increased in a research and development seed production crop in year 6 in the San Joaquin valley where it was designated as uniform and stable while maintaining the desired selected traits of being larger heading and framed, darker color and earlier maturing than its parent variety Sun Devil. The S3 seed of PX 1555 was harvested in bulk in the fall of year 6.

Extensive trialing of the S3 seed of PX 1555 was conducted in August, year 7 in the Huron production region of California and in September, year 7 in Yuma, Ariz. PX 1555 was evaluated on multiple occasions for head and frame size, color, maturity and resistance to tip burn as compared to its parent variety Sun Devil and its sister lines. The S3 generation of the variety PX 1555 continually demonstrated the desired characteristics, being larger heading and framed, darker in color, and slightly earlier maturing than Sun Devil, while maintaining the desired traits of heavy leaf texture, low cores and tip burn resistance.

Based on the continued performance of the variety, an additional and larger seed increase was conducted in a commercial seed production field in San Joaquin Valley, Calif., in year 7. The block was evaluated and rogued at multiple stages of development and deemed to be uniform and stable without variants, while continuing to demonstrate the desired improvement traits. The S4 seed was harvested in the fall of year 7.

Large multiple bed trials of the S4 version of PX 1555 were conducted in year 8 in both the Huron, Calif., and Yuma, Ariz., production regions. PX 1555 was evaluated multiple times compared to its parent line Sun Devil, where it was continually evaluated to be larger heading and framed, darker in color and slightly earlier maturing. The S4 generation of PX 1555 was evaluated to be uniform and stable without variants.

While trials of the variety were being evaluated in December of year 8, the decision was made to advance the variety to commercial level, and PX 1555 was named 'Sun Quest'. An additional and larger increase of the seed was produced in the summer of 2009 in the San Joaquin valley where the S5 seed was rogued at multiple stages of development and noted to be uniform and stable without variants. Sun Quest has been observed in large commercial plantings and in seed production fields to be uniform, stable, and free of variants for 2 generations.

A. Variety Description Information

| | |
|---|---|
| Plant Type: | Iceberg |
| Seed: | |
| Seed Color: | White |
| Light Dormancy: | No |
| Heat Dormancy: | Yes |
| Cotyledons: | |
| Shape of Cotyledons: | Intermediate |
| Shape of Fourth Leaf: | Spatulate |
| Length/Width Index of Fourth Leaf: | 28 |
| Apical Margin: | Finley Dentate |
| Basal Margin: | Finley Dentate |
| Undulation: | Flat |
| Green Color: | Dark |
| Anthocyanin: | Absent |
| Distribution: | None |
| Rolling: | Absent |
| Cupping: | Slight |
| Reflexing: | Slight |
| Mature Leaves: | |
| Margin: | |

-continued

| | |
|---|---|
| Incision Depth (Deepest penetration of the margin): | Deep |
| Indentation (Finest division of the margin): | Shallowly Dentate |
| Undulation of the Apical Margin: | Moderate |
| Green Color: | Dark |
| Anthocyanin Distribution: | None |
| Size: | Large |
| Glossiness: | Moderate |
| Blistering: | Moderate |
| Leaf Thickness: | Thick |
| Trichomes: | Absent |

B. Comparison to Most Similar Variety

| Characteristic | Sun Quest | Sun Devil |
|---|---|---|
| Spread of Frame Leaves | 51 cm | 47 cm |
| Head Diameter (market trimmed with single cup leaf) | 14 cm | 13 cm |
| Head Shape | Spherical | Spherical |
| Head Size Class | Large | Large |
| Head Count per Carton | 24 | 24 |
| Head Weight | 1,068 | 936 |
| Head Firmness | Firm | Firm |
| Butt Shape | Rounded | Rounded |
| Midrib | Moderately Raised | Moderately Raised |
| Core (Stem of market-trimmed head) | | |
| Diameter at the base of the head | 4.5 cm | 4.3 cm |
| Ratio of Head Diameter/Core Diameter | 3.1 | 3.0 |
| Core Height from base of Head to Apex | 3.5 cm | 3.4 cm |
| Number of Days from First Water Date to Seed Stalk Emergence (Summer condition) | 60 | 60 |
| Bolting Class | Slow | Slow |
| Height of Mature Seed Stalk | 132 cm | 126 cm |
| Spread of Bolter Plant | 45 cm | 39 cm |
| Bolter Leaves | Curved | Curved |
| Margin | Dentate | Dentate |
| Color | Dark Green | Medium Green |
| Bolter Habit | | |
| Terminal Inflorescence | Present | Present |
| Lateral Shoots (above head) | Present | Present |
| Basal Side Shoots | Present | Present |
| Adaptation Regions | Huron, CA Yuma, AZ | Huron, CA Yuma, AZ |

C. Growing Season

| Season | Sun Quest | Sun Devil |
|---|---|---|
| Spring area | Not Adapted | Not Adapted |
| Summer area | Not Adapted | Not Adapted |
| Fall area | Desert South West | Desert South West |
| Winter area: | Not Adapted | Not Adapted |

D. Diseases and Stress Reactions

| Disease or Stress | Sun Quest | Sun Devil |
|---|---|---|
| Virus | | |
| Big Vein: | Susceptible | Susceptible |
| Lettuce Mosaic: | Resistant | Resistant |

E. Fungi/Bacteria

| Fungal/Bacterial | Sun Quest | Sun Devil |
|---|---|---|
| Corky Root Rot (*Pythium* Root Rot): | Susceptible | Susceptible |
| Downy Mildew (Races I, IIA, III): | Susceptible | Susceptible |
| Powdery Mildew: | Susceptible | Susceptible |
| Sclerotinia Rot: | Susceptible | Susceptible |
| Bacterial Soft Rot (*Pseudomonas* spp. & others): Not tested | | |
| *Botrytis* (Gray Mold): | Susceptible | Susceptible |
| Other: Corky Root Rot (*Rhizomonas suberifaciens*): | Susceptible | Susceptible |

F. Insects

| Insects | Sun Quest | Sun Devil |
|---|---|---|
| Cabbage Loopers: | Susceptible | Susceptible |
| Root Aphids: | Susceptible | Susceptible |
| Green Peach Aphid: | Susceptible | Susceptible |

G. Physiological/Stress

| Stress | Sun Quest | Sun Devil |
|---|---|---|
| Tipburn | Resistant | Resistant |
| Heat | Resistant | Resistant |
| Drought | Susceptible | Susceptible |
| Cold | Susceptible | Susceptible |
| Salt | Susceptible | Susceptible |

H. Post Harvest

| Characteristic | Sun Quest | Sun Devil |
|---|---|---|
| Pink Rib | Moderately Susceptible | Moderately Susceptible |
| Russet Spotting | Moderately Susceptible | Moderately Susceptible |
| Rusty Brown Discoloration | Moderately Susceptible | Moderately Susceptible |
| Internal Rib Necrosis (Blackheart, Gray Rib, Gray Streak) | Moderately Susceptible | Moderately Susceptible |

Breeding and Selection

The present invention is further directed to the use of Sun Quest lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% selffertilization. Since each lettuce flower is an aggregate of about 10-20 individual florets (typical of the Compositae family), manual removal of the anther tubes containing the pollen may be performed by procedures well known in the art of lettuce breeding.

In addition to manual removal of anther tubes, a modified method of misting to wash the pollen off prior to fertilization may be used to assure crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen are washed off with enough pressure to dislodge the pollen grains, but not enough to damage the style. Excess water is dried off with clean paper towels. About 30 minutes later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the F.sub.2 generations when expected segregation patterns for the genetic character of interest can be followed. This latter situation mandates a lengthy wait to determine if hybrids are produced. Two useful references teaching the methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908.

B. Selection

In addition to crossing, selection may be used to isolate lettuce new lettuce lines. One or more lettuce seeds are planted, the plants are grown and single plant selections are made of plants with desired characteristics. Such characteristics may include, improved head and frame size, deeper or darker green leaf color, etc. Seed from the single plant selections are harvested; separated from seeds of the other plants in the field and re-planted. The plants from the selected seed are monitored to determine if they exhibit the desired characteristics from the originally selected line. Selection work is continued over multiple generations to increase the uniformity and size of new line.

IX. DEPOSIT INFORMATION

Applicants have made available to the public without restriction a deposit of at least 2,500 seeds of lettuce variety Sun Quest with the American Type Culture Collection (ATCC), 10801 University Boulevard, Manassas, Va. 20110 USA with a deposit on Apr. 4, 2011 which has been assigned ATCC number PTA-11798.

The deposit will be maintained in the ATCC depository, which is a public depository, for a period of 30 years, or 5 years after the most recent request, or for the effective life of the patent, whichever is longer, and will be replaced if a deposit becomes non-viable during that period.

This invention will be better understood by reference to the following non-limiting Examples.

Example 1

General Trialing Method

I. Set Up
1. Parental lines and competing varieties are identified.
2. Primary slots are identified.
3. Necessary accession lines are located and purchased/received from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting, and the necessary rows and area is marked off.
3. Varieties are planted according to a diagram in 100 ft. ranges.
4. All varieties are planted in same manner to mimic the planting of the commercial variety as closely as possible.
5. A trial map is drawn diagramming the trial, the trial location in the field and directions to the field.

III. Maintenance
1. All varieties are treated identically. Plants are watered, fertilized, and treated to control pests in the same manner as the commercial field.
2. The trial is thinned to separate the plants for optimum growth.

Example 2

Comparative Analysis

Following the procedures of Example 1, Sun Quest iceberg lettuce was compared to its most similar variety. The data are presented in Tables 1 and 2. Table 1 shows trial data comparing the head diameter of Sun Devil and Sun Quest iceberg lettuce varieties. Table 2 shows trial data comparing the frame diameter of Sun Devil and Sun Quest iceberg lettuce varieties.

Sun Quest is a new and distinct variety of iceberg lettuce that most closely resembles the commercial variety Sun Devil. Sun Quest is a vanguard type iceberg lettuce variety adapted to the fall harvest of the desert southwest and Huron lettuce production regions of California and Arizona. Sun Quest is a large heading and large framed variety, with excellent heading characteristics, leaf texture and improved resistance to tip burn and bolting.

Sun Quest is a larger heading and larger framed than Sun Devil, and is more uniform in head size and maturity. Sun Quest is also one to two days earlier maturing than Sun Devil. Similar to Sun Devil, Sun Quest is adapted to the fall harvest in the desert south west production region, and has maintained the heavy leaf texture, slow bolting and excellent tip burn resistance of its parent.

Sun Quest is distinguished from Sun Devil by the following characteristics as represented in Tables 1 and 2.

Sun Quest has a significantly larger head diameter than Sun Devil.

Sun Quest has a significantly larger frame diameter than Sun Devil.

This data is represented in Tables 1 and 2, and are statistically significant at the 95% confidence level, exhibiting a range of means for head diameter from 128.9 to 141.4 mm for Sun Quest and from 123.1 to 134.3 mm for Sun Devil, and for frame diameter, from 50.1 to 51.7 cm for Sun Quest and ranging from 46.8 to 48.5 cm for Sun Devil.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

TABLE 1

Evaluation of Sun Quest and the most similar cultivar Sun Devil for head diameter measured to the nearest 1 mm.

| Trial No. | SYM08307 | | SYM08312 | | SYM08363 | |
|---|---|---|---|---|---|---|
| Wet/Eval Date | Sep. 13, 2008 | Nov. 27, 2008 | Sep. 14, 2008 | Nov. 28, 2008 | Sep. 17, 2008 | Dec. 2, 2008 |
| Location | Yuma Az | | Yuma Az | | Yuma Az | |
| | Head Diam. (mm) | | Head Diam. (mm) | | Head Diam. (mm) | |
| Plant | Sun Quest | Sun Devil | Sun Quest | Sun Devil | Sun Quest | Sun Devil |
| 1 | 128.0 | 125.0 | 133.0 | 122.0 | 135.0 | 130.0 |
| 2 | 133.0 | 126.0 | 138.0 | 125.0 | 136.0 | 130.0 |
| 3 | 136.0 | 125.0 | 135.0 | 124.0 | 136.0 | 131.0 |
| 4 | 135.0 | 128.0 | 136.0 | 126.0 | 136.0 | 135.0 |
| 5 | 133.0 | 130.0 | 136.0 | 129.0 | 138.0 | 130.0 |
| 6 | 132.0 | 126.0 | 134.0 | 130.0 | 138.0 | 130.0 |
| 7 | 138.0 | 130.0 | 135.0 | 130.0 | 139.0 | 129.0 |
| 8 | 135.0 | 124.0 | 136.0 | 130.0 | 136.0 | 128.0 |
| 9 | 136.0 | 126.0 | 136.0 | 125.0 | 135.0 | 132.0 |
| 10 | 129.0 | 135.0 | 139.0 | 126.0 | 136.0 | 130.0 |
| 11 | 128.0 | 120.0 | 135.0 | 129.0 | 134.0 | 125.0 |
| 12 | 133.0 | 125.0 | 129.0 | 125.0 | 130.0 | 125.0 |
| 13 | 133.0 | 135.0 | 125.0 | 125.0 | 132.0 | 126.0 |
| 14 | 135.0 | 123.0 | 136.0 | 125.0 | 130.0 | 124.0 |
| 15 | 134.0 | 135.0 | 127.0 | 135.0 | 125.0 | 125.0 |
| 16 | 139.0 | 130.0 | 136.0 | 132.0 | 133.0 | 130.0 |
| 17 | 127.0 | 130.0 | 135.0 | 134.0 | 134.0 | 130.0 |
| 18 | 125.0 | 130.0 | 133.0 | 130.0 | 132.0 | 131.0 |
| 19 | 136.0 | 124.0 | 125.0 | 125.0 | 135.0 | 132.0 |
| 20 | 139.0 | 125.0 | 128.0 | 129.0 | 132.0 | 135.0 |
| 21 | 138.0 | 123.0 | 135.0 | 125.0 | 133.0 | 136.0 |
| 22 | 134.0 | 126.0 | 136.0 | 130.0 | 135.0 | 130.0 |
| 23 | 133.0 | 128.0 | 129.0 | 125.0 | 139.0 | 125.0 |
| 24 | 136.0 | 123.0 | 130.0 | 128.0 | 136.0 | 124.0 |
| 25 | 135.0 | 129.0 | 130.0 | 123.0 | 134.0 | 124.0 |
| 26 | 135.0 | 125.0 | 135.0 | 127.0 | 133.0 | 120.0 |
| 27 | 133.0 | 125.0 | 125.0 | 128.0 | 134.0 | 125.0 |
| 28 | 132.0 | 120.0 | 124.0 | 126.0 | 135.0 | 126.0 |
| 29 | 132.0 | 123.0 | 129.0 | 130.0 | 130.0 | 123.0 |
| 30 | 135.0 | 135.0 | 136.0 | 132.0 | 136.0 | 120.0 |
| Average | 133.6 | 127.0 | 132.5 | 127.7 | 134.2 | 128.0 |
| Stan dev | 3.44E+00 | 4.21E+00 | 4.36E+00 | 3.23E+00 | 2.98E+00 | 4.15E+00 |
| T test | 6.45E−04 | | 7.73E−06 | | 1.13E−08 | |
| Probability % | 99.9 | | 99.9992 | | 100.0000 | |
| % Difference | 5.2 | | 3.8 | | 4.8 | |
| Confidence Int | 0.0394 | 0.0482 | 0.0499 | 0.0370 | 0.0341 | 0.0475 |
| Range of Var min* | 133.53 | 126.92 | 132.48 | 127.63 | 134.20 | 127.99 |
| Range of Var max* | 133.61 | 127.01 | 132.58 | 127.70 | 134.27 | 128.08 |

| Trial No. | SYM09291 | | SYM09292 | | SYM09304 | |
|---|---|---|---|---|---|---|
| Wet/Eval Date | Sep. 13, 2009 | Nov. 24, 2009 | Sep. 14, 2009 | Nov. 26, 2009 | Sep. 18, 2009 | Dec. 2, 2009 |
| Location | Yuma Az | | Yuma Az | | Yuma Az | |
| | Head Diam. (mm) | | Head Diam. (mm) | | Head Diam. (mm) | |
| Plant | Sun Quest | Sun Devil | Sun Quest | Sun Devil | Sun Quest | Sun Devil |
| 1 | 129.0 | 120.0 | 139.0 | 130.0 | 139.0 | 130.0 |
| 2 | 128.0 | 120.0 | 139.0 | 130.0 | 139.0 | 130.0 |
| 3 | 124.0 | 119.0 | 141.0 | 135.0 | 138.0 | 132.0 |
| 4 | 126.0 | 120.0 | 145.0 | 135.0 | 135.0 | 135.0 |
| 5 | 129.0 | 120.0 | 142.0 | 135.0 | 135.0 | 135.0 |
| 6 | 123.0 | 124.0 | 142.0 | 134.0 | 135.0 | 135.0 |
| 7 | 130.0 | 125.0 | 145.0 | 139.0 | 135.0 | 130.0 |
| 8 | 130.0 | 120.0 | 148.0 | 135.0 | 135.0 | 132.0 |
| 9 | 134.0 | 120.0 | 146.0 | 139.0 | 140.0 | 130.0 |
| 10 | 131.0 | 129.0 | 139.0 | 134.0 | 142.0 | 129.0 |
| 11 | 132.0 | 118.0 | 139.0 | 137.0 | 135.0 | 128.0 |
| 12 | 135.0 | 123.0 | 145.0 | 139.0 | 142.0 | 128.0 |
| 13 | 132.0 | 124.0 | 135.0 | 135.0 | 142.0 | 127.0 |
| 14 | 131.0 | 125.0 | 139.0 | 135.0 | 135.0 | 125.0 |
| 15 | 136.0 | 123.0 | 140.0 | 138.0 | 136.0 | 130.0 |
| 16 | 130.0 | 120.0 | 142.0 | 136.0 | 139.0 | 125.0 |
| 17 | 125.0 | 125.0 | 140.0 | 136.0 | 140.0 | 125.0 |
| 18 | 121.0 | 124.0 | 147.0 | 139.0 | 145.0 | 136.0 |

TABLE 1-continued

Evaluation of Sun Quest and the most similar cultivar Sun Devil for head diameter measured to the nearest 1 mm.

| | | | | | | |
|---|---|---|---|---|---|---|
| 19 | 125.0 | 129.0 | 139.0 | 125.0 | 145.0 | 125.0 |
| 20 | 120.0 | 120.0 | 135.0 | 120.0 | 143.0 | 129.0 |
| 21 | 120.0 | 127.0 | 135.0 | 129.0 | 135.0 | 128.0 |
| 22 | 125.0 | 123.0 | 142.0 | 136.0 | 139.0 | 130.0 |
| 23 | 126.0 | 126.0 | 148.0 | 128.0 | 130.0 | 130.0 |
| 24 | 129.0 | 120.0 | 146.0 | 135.0 | 134.0 | 135.0 |
| 25 | 130.0 | 120.0 | 140.0 | 134.0 | 135.0 | 134.0 |
| 26 | 130.0 | 125.0 | 146.0 | 127.0 | 140.0 | 136.0 |
| 27 | 133.0 | 126.0 | 139.0 | 139.0 | 142.0 | 130.0 |
| 28 | 134.0 | 130.0 | 137.0 | 139.0 | 145.0 | 132.0 |
| 29 | 136.0 | 120.0 | 140.0 | 140.0 | 143.0 | 134.0 |
| 30 | 135.0 | 130.0 | 142.0 | 135.0 | 144.0 | 133.0 |
| Average | 129.0 | 123.2 | 141.4 | 134.3 | 138.7 | 130.6 |
| Stan dev | 4.63E+00 | 3.53E+00 | 3.77E+00 | 4.73E+00 | 3.99E+00 | 3.41E+00 |
| T test | 1.05E−06 | | 2.36E−08 | | 9.41E−12 | |
| Probability % | 99.9999 | | 100.0000 | | 100.0000 | |
| % Difference | 4.7 | | 5.3 | | 6.2 | |
| Confidence Int | 0.0530 | 0.0405 | 0.0432 | 0.0541 | 0.0457 | 0.0390 |
| Range of Var min* | 128.91 | 123.13 | 141.36 | 134.21 | 138.69 | 130.56 |
| Range of Var max* | 129.02 | 123.21 | 141.44 | 134.32 | 138.78 | 130.64 |

*Range of variation among means of statistically significant differences at the 95% level using the confidence interval

[C] = mean +/− {SDXSE}

TABLE 2

Evaluation of Sun Quest and the most similar cultivar Sun Devil for frame diameter measured to the nearest 1 cm.

| Trial No. | SYM08307 | | SYM08312 | | SYM08363 | |
|---|---|---|---|---|---|---|
| Wet/Eval Date | Sep. 13, 2008 | Nov. 27, 2008 | Sep. 14, 2008 | Nov. 28, 2008 | Sep. 17, 2008 | Dec. 2, 2008 |
| Location | Yuma Az | | Yuma Az | | Yuma Az | |
| | Frame Diam. (cm) | | Frame Diam. (cm) | | Frame Diam. (cm) | |
| Plant | Sun Quest | Sun Devil | Sun Quest | Sun Devil | Sun Quest | Sun Devil |
| 1 | 48.0 | 46.0 | 52.0 | 49.0 | 51.0 | 49.0 |
| 2 | 51.0 | 46.0 | 51.0 | 49.0 | 53.0 | 49.0 |
| 3 | 52.0 | 47.0 | 52.0 | 45.0 | 53.0 | 47.0 |
| 4 | 50.0 | 49.0 | 52.0 | 49.0 | 54.0 | 46.0 |
| 5 | 50.0 | 49.0 | 50.0 | 51.0 | 51.0 | 45.0 |
| 6 | 55.0 | 50.0 | 50.0 | 51.0 | 50.0 | 45.0 |
| 7 | 54.0 | 50.0 | 50.0 | 52.0 | 50.0 | 45.0 |
| 8 | 52.0 | 50.0 | 54.0 | 49.0 | 59.0 | 42.0 |
| 9 | 54.0 | 51.0 | 50.0 | 48.0 | 53.0 | 49.0 |
| 10 | 52.0 | 47.0 | 52.0 | 49.0 | 53.0 | 49.0 |
| 11 | 52.0 | 45.0 | 57.0 | 49.0 | 52.0 | 48.0 |
| 12 | 52.0 | 45.0 | 53.0 | 50.0 | 49.0 | 45.0 |
| 13 | 53.0 | 45.0 | 52.0 | 51.0 | 48.0 | 45.0 |
| 14 | 50.0 | 46.0 | 50.0 | 51.0 | 47.0 | 45.0 |
| 15 | 50.0 | 46.0 | 51.0 | 51.0 | 50.0 | 45.0 |
| 16 | 49.0 | 47.0 | 54.0 | 50.0 | 50.0 | 49.0 |
| 17 | 48.0 | 42.0 | 54.0 | 50.0 | 51.0 | 51.0 |
| 18 | 46.0 | 45.0 | 52.0 | 50.0 | 51.0 | 51.0 |
| 19 | 48.0 | 43.0 | 58.0 | 49.0 | 50.0 | 49.0 |
| 20 | 49.0 | 46.0 | 53.0 | 48.0 | 52.0 | 50.0 |
| 21 | 50.0 | 46.0 | 50.0 | 46.0 | 52.0 | 52.0 |
| 22 | 50.0 | 48.0 | 50.0 | 46.0 | 49.0 | 49.0 |
| 23 | 48.0 | 50.0 | 49.0 | 47.0 | 50.0 | 49.0 |
| 24 | 53.0 | 51.0 | 50.0 | 50.0 | 50.0 | 46.0 |
| 25 | 42.0 | 49.0 | 51.0 | 47.0 | 53.0 | 48.0 |
| 26 | 50.0 | 46.0 | 48.0 | 46.0 | 54.0 | 45.0 |
| 27 | 50.0 | 46.0 | 47.0 | 50.0 | 49.0 | 46.0 |
| 28 | 50.0 | 47.0 | 50.0 | 42.0 | 48.0 | 49.0 |
| 29 | 49.0 | 48.0 | 52.0 | 43.0 | 50.0 | 46.0 |
| 30 | 48.0 | 49.0 | 51.0 | 45.0 | 54.0 | 46.0 |
| Average | 50.2 | 47.2 | 51.5 | 48.4 | 51.2 | 47.3 |
| Stan dev | 2.61E+00 | 2.28E+00 | 2.33E+00 | 2.49E+00 | 2.40E+00 | 2.37E+00 |
| T test | 1.63E−03 | | 7.28E−06 | | 4.63E−08 | |
| Probability % | 99.8 | | 99.9993 | | 100.0000 | |
| % Difference | 6.4 | | 6.3 | | 8.2 | |
| Confidence Int | 0.0299 | 0.0261 | 0.0267 | 0.0285 | 0.0275 | 0.0271 |
| Range of Var min* | 50.14 | 47.14 | 51.47 | 48.40 | 51.17 | 47.31 |
| Range of Var max* | 50.20 | 47.19 | 51.53 | 48.46 | 51.23 | 47.36 |

TABLE 2-continued

Evaluation of Sun Quest and the most similar cultivar Sun Devil for frame diameter measured to the nearest 1 cm.

| Trial No. | SYM09291 | | SYM09292 | | SYM09304 | |
|---|---|---|---|---|---|---|
| Wet/Eval Date | Sep. 13, 2009 | Nov. 24, 2009 | Sep. 14, 2009 | Nov. 26, 2009 | Sep. 18, 2009 | Dec. 2, 2009 |
| Location | Yuma Az | | Yuma Az | | Yuma Az | |
| | Frame Diam. (cm) | | Frame Diam. (cm) | | Frame Diam. (cm) | |
| Plant | Sun Quest | Sun Devil | Sun Quest | Sun Devil | Sun Quest | Sun Devil |
| 1 | 53.0 | 49.0 | 52.0 | 49.0 | 49.0 | 49.0 |
| 2 | 55.0 | 49.0 | 52.0 | 48.0 | 48.0 | 48.0 |
| 3 | 51.0 | 49.0 | 54.0 | 49.0 | 45.0 | 48.0 |
| 4 | 51.0 | 46.0 | 52.0 | 49.0 | 49.0 | 46.0 |
| 5 | 54.0 | 50.0 | 50.0 | 48.0 | 52.0 | 46.0 |
| 6 | 54.0 | 46.0 | 55.0 | 45.0 | 52.0 | 45.0 |
| 7 | 51.0 | 45.0 | 56.0 | 45.0 | 56.0 | 49.0 |
| 8 | 50.0 | 42.0 | 58.0 | 45.0 | 55.0 | 50.0 |
| 9 | 49.0 | 49.0 | 51.0 | 46.0 | 50.0 | 50.0 |
| 10 | 48.0 | 49.0 | 51.0 | 46.0 | 50.0 | 48.0 |
| 11 | 50.0 | 45.0 | 51.0 | 49.0 | 51.0 | 47.0 |
| 12 | 54.0 | 45.0 | 50.0 | 51.0 | 51.0 | 48.0 |
| 13 | 56.0 | 46.0 | 50.0 | 51.0 | 51.0 | 46.0 |
| 14 | 52.0 | 42.0 | 52.0 | 48.0 | 52.0 | 46.0 |
| 15 | 52.0 | 43.0 | 53.0 | 48.0 | 53.0 | 45.0 |
| 16 | 53.0 | 45.0 | 53.0 | 50.0 | 53.0 | 48.0 |
| 17 | 56.0 | 45.0 | 52.0 | 50.0 | 54.0 | 45.0 |
| 18 | 49.0 | 45.0 | 54.0 | 49.0 | 49.0 | 45.0 |
| 19 | 50.0 | 48.0 | 49.0 | 48.0 | 51.0 | 50.0 |
| 20 | 50.0 | 49.0 | 49.0 | 48.0 | 50.0 | 51.0 |
| 21 | 53.0 | 45.0 | 51.0 | 48.0 | 49.0 | 49.0 |
| 22 | 49.0 | 46.0 | 48.0 | 46.0 | 52.0 | 51.0 |
| 23 | 48.0 | 45.0 | 53.0 | 49.0 | 52.0 | 48.0 |
| 24 | 47.0 | 46.0 | 49.0 | 51.0 | 53.0 | 51.0 |
| 25 | 50.0 | 46.0 | 53.0 | 51.0 | 49.0 | 51.0 |
| 26 | 51.0 | 49.0 | 53.0 | 46.0 | 47.0 | 49.0 |
| 27 | 54.0 | 49.0 | 49.0 | 46.0 | 50.0 | 48.0 |
| 28 | 49.0 | 51.0 | 51.0 | 49.0 | 51.0 | 49.0 |
| 29 | 51.0 | 51.0 | 48.0 | 48.0 | 48.0 | 50.0 |
| 30 | 48.0 | 49.0 | 50.0 | 45.0 | 53.0 | 50.0 |
| Average | 51.3 | 46.8 | 51.6 | 48.0 | 50.8 | 48.2 |
| Stan dev | 2.43E+00 | 2.50E+00 | 2.34E+00 | 1.92E+00 | 2.38E+00 | 1.97E+00 |
| T test | 3.47E−09 | | 1.93E−08 | | 1.85E−05 | |
| Probability % | 100.0000 | | 100.0000 | | 99.9982 | |
| % Difference | 9.5 | | 7.5 | | 5.5 | |
| Confidence Int | 0.0284 | 0.0286 | 0.0268 | 0.0220 | 0.0272 | 0.0226 |
| Range of Var min* | 51.24 | 46.77 | 51.61 | 48.01 | 50.81 | 48.18 |
| Range of Var max* | 51.30 | 46.83 | 51.66 | 48.06 | 50.83 | 48.22 |

| Trial No. | SYM08307 | | SYM08312 | | SYM08363 | |
|---|---|---|---|---|---|---|
| Wet/Eval Date | Sep. 13, 2008 | Nov. 27, 2008 | Sep. 14, 2008 | Nov. 28, 2008 | Sep. 17, 2008 | Dec. 2, 2008 |
| Location | Yuma Az | | Yuma Az | | Yuma Az | |
| | Frame Diam. (cm) | | Frame Diam. (cm) | | Frame Diam. (cm) | |
| Plant | Sun Quest | Sun Devil | Sun Quest | Sun Devil | Sun Quest | Sun Devil |
| 1 | 48.0 | 46.0 | 52.0 | 49.0 | 51.0 | 49.0 |
| 2 | 51.0 | 46.0 | 51.0 | 49.0 | 53.0 | 49.0 |
| 3 | 52.0 | 47.0 | 52.0 | 45.0 | 53.0 | 47.0 |
| 4 | 50.0 | 49.0 | 52.0 | 49.0 | 54.0 | 46.0 |
| 5 | 50.0 | 49.0 | 50.0 | 51.0 | 51.0 | 45.0 |
| 6 | 55.0 | 50.0 | 50.0 | 51.0 | 50.0 | 45.0 |
| 7 | 54.0 | 50.0 | 50.0 | 52.0 | 50.0 | 45.0 |
| 8 | 52.0 | 50.0 | 54.0 | 49.0 | 59.0 | 42.0 |
| 9 | 54.0 | 51.0 | 50.0 | 48.0 | 53.0 | 49.0 |
| 10 | 52.0 | 47.0 | 52.0 | 49.0 | 53.0 | 49.0 |
| 11 | 52.0 | 45.0 | 57.0 | 49.0 | 52.0 | 48.0 |
| 12 | 52.0 | 45.0 | 53.0 | 50.0 | 49.0 | 45.0 |
| 13 | 53.0 | 45.0 | 52.0 | 51.0 | 48.0 | 45.0 |
| 14 | 50.0 | 46.0 | 50.0 | 51.0 | 47.0 | 45.0 |
| 15 | 50.0 | 46.0 | 51.0 | 51.0 | 50.0 | 45.0 |
| 16 | 49.0 | 47.0 | 54.0 | 50.0 | 50.0 | 49.0 |
| 17 | 48.0 | 42.0 | 54.0 | 50.0 | 51.0 | 51.0 |
| 18 | 46.0 | 45.0 | 52.0 | 50.0 | 51.0 | 51.0 |
| 19 | 48.0 | 43.0 | 58.0 | 49.0 | 50.0 | 49.0 |
| 20 | 49.0 | 46.0 | 53.0 | 48.0 | 52.0 | 50.0 |
| 21 | 50.0 | 46.0 | 50.0 | 46.0 | 52.0 | 52.0 |
| 22 | 50.0 | 48.0 | 50.0 | 46.0 | 49.0 | 49.0 |
| 23 | 48.0 | 50.0 | 49.0 | 47.0 | 50.0 | 49.0 |
| 24 | 53.0 | 51.0 | 50.0 | 50.0 | 50.0 | 46.0 |
| 25 | 42.0 | 49.0 | 51.0 | 47.0 | 53.0 | 48.0 |

TABLE 2-continued

Evaluation of Sun Quest and the most similar cultivar Sun Devil for frame diameter measured to the nearest 1 cm.

| | | | | | | |
|---|---|---|---|---|---|---|
| 26 | 50.0 | 46.0 | 48.0 | 46.0 | 54.0 | 45.0 |
| 27 | 50.0 | 46.0 | 47.0 | 50.0 | 49.0 | 46.0 |
| 28 | 50.0 | 47.0 | 50.0 | 42.0 | 48.0 | 49.0 |
| 29 | 49.0 | 48.0 | 52.0 | 43.0 | 50.0 | 46.0 |
| 30 | 48.0 | 49.0 | 51.0 | 45.0 | 54.0 | 46.0 |
| Average | 50.2 | 47.2 | 51.5 | 48.4 | 51.2 | 47.3 |
| Stan dev | 2.61E+00 | 2.28E+00 | 2.33E+00 | 2.49E+00 | 2.40E+00 | 2.37E+00 |
| T test | 1.69E−03 | | 7.28E−06 | | 4.63E−08 | |
| Probability % | 99.8 | | 99.9993 | | 100.0000 | |
| % Difference | 6.4 | | 6.3 | | 8.2 | |
| Confidence Int | 0.0299 | 0.0261 | 0.0267 | 0.0285 | 0.0275 | 0.0271 |
| Range of Var min* | 50.14 | 47.14 | 51.47 | 48.40 | 51.17 | 47.31 |
| Range of Var max* | 50.20 | 47.19 | 51.53 | 48.46 | 51.23 | 47.36 |

| Trial No. | SYM09291 | | SYM09292 | | SYM09304 | |
|---|---|---|---|---|---|---|
| Wet/Eval Date | Sep. 13, 2009 | Nov. 24, 2009 | Sep. 14, 2009 | Nov. 26, 2009 | Sep. 18, 2009 | Dec. 2, 2009 |
| Location | Yuma Az | | Yuma Az | | Yuma Az | |
| | Frame Diam. (cm) | | Frame Diam. (cm) | | Frame Diam. (cm) | |
| Plant | Sun Quest | Sun Devil | Sun Quest | Sun Devil | Sun Quest | Sun Devil |
| 1 | 53.0 | 49.0 | 52.0 | 49.0 | 49.0 | 49.0 |
| 2 | 55.0 | 49.0 | 52.0 | 48.0 | 48.0 | 48.0 |
| 3 | 51.0 | 49.0 | 54.0 | 49.0 | 45.0 | 48.0 |
| 4 | 51.0 | 46.0 | 52.0 | 49.0 | 49.0 | 46.0 |
| 5 | 54.0 | 50.0 | 50.0 | 48.0 | 52.0 | 46.0 |
| 6 | 54.0 | 46.0 | 55.0 | 45.0 | 52.0 | 45.0 |
| 7 | 51.0 | 45.0 | 56.0 | 45.0 | 56.0 | 49.0 |
| 8 | 50.0 | 42.0 | 58.0 | 45.0 | 55.0 | 50.0 |
| 9 | 49.0 | 49.0 | 51.0 | 46.0 | 50.0 | 50.0 |
| 10 | 48.0 | 49.0 | 51.0 | 46.0 | 50.0 | 48.0 |
| 11 | 50.0 | 45.0 | 51.0 | 49.0 | 51.0 | 47.0 |
| 12 | 54.0 | 45.0 | 50.0 | 51.0 | 51.0 | 48.0 |
| 13 | 56.0 | 46.0 | 50.0 | 51.0 | 51.0 | 46.0 |
| 14 | 52.0 | 42.0 | 52.0 | 48.0 | 52.0 | 46.0 |
| 15 | 52.0 | 43.0 | 53.0 | 48.0 | 53.0 | 45.0 |
| 16 | 53.0 | 45.0 | 53.0 | 50.0 | 53.0 | 48.0 |
| 17 | 56.0 | 45.0 | 52.0 | 50.0 | 54.0 | 45.0 |
| 18 | 49.0 | 45.0 | 54.0 | 49.0 | 49.0 | 45.0 |
| 19 | 50.0 | 48.0 | 49.0 | 48.0 | 51.0 | 50.0 |
| 20 | 50.0 | 49.0 | 49.0 | 48.0 | 50.0 | 51.0 |
| 21 | 53.0 | 45.0 | 51.0 | 48.0 | 49.0 | 49.0 |
| 22 | 49.0 | 46.0 | 48.0 | 46.0 | 52.0 | 51.0 |
| 23 | 48.0 | 45.0 | 53.0 | 49.0 | 52.0 | 48.0 |
| 24 | 47.0 | 46.0 | 49.0 | 51.0 | 53.0 | 51.0 |
| 25 | 50.0 | 46.0 | 53.0 | 51.0 | 49.0 | 51.0 |
| 26 | 51.0 | 49.0 | 53.0 | 46.0 | 47.0 | 49.0 |
| 27 | 54.0 | 49.0 | 49.0 | 46.0 | 50.0 | 48.0 |
| 28 | 49.0 | 51.0 | 51.0 | 49.0 | 51.0 | 49.0 |
| 29 | 51.0 | 51.0 | 48.0 | 48.0 | 48.0 | 50.0 |
| 30 | 48.0 | 49.0 | 50.0 | 45.0 | 53.0 | 50.0 |
| Average | 51.3 | 46.8 | 51.6 | 48.0 | 50.8 | 48.2 |
| Stan dev | 2.48E+00 | 2.50E+00 | 2.34E+00 | 1.92E+00 | 2.38E+00 | 1.97E+00 |
| T test | 3.47E−09 | | 1.93E−08 | | 1.85E−05 | |
| Probability % | 100.0000 | | 100.0000 | | 99.9982 | |
| % Difference | 9.5 | | 7.5 | | 5.5 | |
| Confidence Int | 0.0284 | 0.0268 | 0.0268 | 0.0220 | 0.0272 | 0.0226 |
| Range of Var min* | 51.24 | 46.77 | 51.61 | 48.01 | 50.81 | 48.18 |
| Range of Var max* | 51.30 | 46.83 | 51.66 | 48.06 | 50.86 | 48.22 |

*Range of variation among means of statistically significant differences at the 95% level using the confidence interval
[C] = mean +/− {SDXSE}

I claim:

1. *Lactuca sativa* seed designated as Sun Quest having ATCC Accession Number PTA-11798.

2. A *Lactuca sativa* plant produced by growing the seed of claim 1.

3. A *Lactuca sativa* plant having all the physiological and morphological characteristics of the *Lactuca sativa* plant of claim 2.

4. A $F_1$ hybrid *Lactuca sativa* plant having Sun Quest as a parent where Sun Quest is grown from the seed of claim 1.

5. Pollen of the plant of claim 2.

6. Tissue culture of the plant of claim 2.

7. A method of selecting lettuce, comprising:
   a) growing more than one plant from the seed of claim 1
   b) selecting a plant from step a).

* * * * *